United States Patent [19]

Fahim

[11] Patent Number: 5,070,080
[45] Date of Patent: Dec. 3, 1991

[54] METHOD OF INHIBITING GENERATION, MATURATION, MOTILITY AND VIABILITY OF SPERM WITH MINERALS IN BIOAVAILABLE FORM

[76] Inventor: Mostafa S. Fahim, 500 Hulen Dr., Columbia, Mo. 65203

[21] Appl. No.: 303,747

[22] Filed: Jan. 30, 1989

Related U.S. Application Data

[63] Continuation-in-part of Ser. No. 230,582, Aug. 10, 1988, Pat. No. 4,937,234.

[51] Int. Cl.⁵ ................ A61K 31/715; A61K 31/415; A61K 31/315; A61K 31/195
[52] U.S. Cl. ......................... 514/53; 514/400; 514/494; 514/561; 514/564; 514/565
[58] Field of Search ............... 514/970, 561, 53, 356, 514/365, 423, 494, 400, 564, 565; 424/641, 642, 643

[56] References Cited

U.S. PATENT DOCUMENTS

| | | | |
|---|---|---|---|
| 4,339,438 | 7/1982 | Fahim | 424/641 |
| 4,684,528 | 8/1987 | Godfrey | 424/641 |
| 4,863,898 | 9/1989 | Ashmead et al. | 514/6 |
| 4,937,234 | 6/1990 | Fahim | 514/565 |
| 4,956,385 | 9/1990 | Eby | 424/641 |

FOREIGN PATENT DOCUMENTS 0132821 2/1985 European Pat. Off. .

OTHER PUBLICATIONS

Chem. Abstracts 74(9):40226n, Rosado et al. (1970).
Chem. Abstracts 95(23):198271s, Aonuma et al.

*Primary Examiner*—Frederick E. Waddell
*Assistant Examiner*—Raymond J. Henley, III
*Attorney, Agent, or Firm*—Grace J. Fishel

[57] ABSTRACT

A cell permeable physiologically acceptable water soluble mineral salt of a carboxylic acid such as zinc acetate, calcium acetate, zinc gluconate and the like having a pH in the range of 6.0 to 7.5 capable of forming a stable solution under ambient conditions at pH 7.0 is bioavailably effective at inhibiting the generation, maturation, motility and viability of sperm when applied to sperm or developing sperm in the testis, epididymis or vas deferens of a male subject or the vagina, cervix, uterus or fallopian tubes of a female subject. When the subject is a male subject and the mineral salt is zinc gluconate or the like and is injected into the testis or epididymis, the stability and efficacy of the mineral salt at pH 7.0 is improved by the presence of an amino acid such as arginine which acts as a permeation enhancer.

15 Claims, 1 Drawing Sheet

CONTROL EPIDIDYMIS

TREATED EPIDIDYMIS WITH
0.05 ML ZINC GLUCONATE
+ ARGININE 0.1M

METHOD OF INHIBITING GENERATION, MATURATION, MOTILITY AND VIABILITY OF SPERM WITH MINERALS IN BIOAVAILABLE FORM

This application is a continuation-in-part of application Ser. No. 230,582, filed Aug. 10, 1988, for Minerals in Bioavailable Form which is now U.S. Pat. No. 4,937,234.

BACKGROUND OF THE INVENTION

The present invention relates to a method of contraception and compositions useful therefor that are applicable to males and females wherein the generation, maturation, motility and viability of sperm is affected by direct application of minerals in bioavailable form to the sperm or developing sperm in the target organ. Direct application of minerals in bioavailable form avoids the side effects found with other methods which rely on hormones or from the passage of a drug through the digestive tract.

Various water soluble minerals are toxic to sperm and have been injected into the testis or epididymis and been found effective at inhibiting the generation or maturation of sperm in the seminiferous or epididymal epithelium. They have also been found effective in vitro at inhibiting sperm motility and viability and postulated as a vaginal, cervical, uterine or tubal contraceptive in females. These methods, however, have not been put into commercial use because of certain adverse side effects.

To avoid adverse side effects in vivo, lower levels of less toxic materials are clearly preferred. To be effective and avoid hurting the subject, however, such materials must be in a form which is physiologically acceptable and cell permeable. Most water soluble minerals such as zinc chloride, zinc sulfate, zinc tannate and the like have proved too acidic to be commercially acceptable and cannot be neutralized with sodium hydroxide or sodium bicarbonate without effecting the stability of the solution or introducing an unacceptable level of sodium or other counterion.

In view of the above, it is an object of the present invention to provide a class of cell permeable physiologically acceptable water soluble minerals which are effective at inhibiting generation, maturation, motility and viability of sperm when applied in the testis, epididymis or vas deferens or in the vagina, cervix, uterus or fallopian tubes and which are not too acidic, caustic or astringent to cause discomfort to the subject. Other objects and features will be in part apparent and in part pointed out hereinafter. The invention accordingly comprises the methods and compositions hereinafter described and equivalents thereof, the scope of the invention being indicated by the subjoined claims.

SUMMARY OF THE INVENTION

A cell permeable physiologically acceptable water soluble mineral salt of a carboxylic acid having a pH in the range of 6.0 to 7.5 and capable of forming a stable solution under ambient conditions at pH 7.0 is bioavailably effective at inhibiting the generation, maturation, motility and viability of sperm when applied to sperm or developing sperm in a male or female reproductive track. In some instances, the stability and efficacy of the mineral salt at pH 7.0 is improved by the presence of an amino acid such as the basic amino acids arginine, lysine and histidine which acts as a permeation enhancer.

DESCRIPTION OF THE PREFERRED EMBODIMENTS

Figure 1:
FIG. 1 is a histology photograph of an epididymal section from a control animal; and, FIG. 2 is a histology photograph of an epididymal section from an animal treated in accordance with the present invention in Example 1.

In accordance with the present invention a cell permeable physiologically acceptable water soluble mineral is applied to sperm or developing sperm in the testis, epididymis or vas deferens of a male subject or the vagina, cervix, uterus or fallopian tubes of a female subject in an effective amount for inhibiting generation, maturation, motility or viability of the sperm. When applied to the epididymis, the mineral salt does not affect the production of testosterone and therefore does not influence the subject's secondary sex characteristics or libido. In the testis, on the other hand, the mineral decreases testosterone production at higher concentrations. Suitable materials for this purpose are mineral salts of a carboxylic acid having a pH in the range of 6.0 to 7.5 and capable of forming a stable solution under ambient conditions at pH 7.0. Physiologically acceptable minerals include zinc, calcium, iron, magnesium, manganese and the like and illustrative mineral salts include zinc acetate, calcium acetate and the mineral salts of a carboxylic acid derivative of a pentose or hexose such as zinc gluconate or zinc gulonate.

Depending on the target organ, the stability and efficacy of the mineral salt is improved in the presence of an amino acid. With zinc gluconate, it has been discovered that it can be neutralized in the presence of the following amino acids: alanine, valine, isoleucine, proline, glycine, serine, threonine, asparagine, glutamine, lysine, arginine, histidine and mixtures thereof. The adjustment cannot be made with cysteine, tyrosine, aspartic acid or glutamic acid and among the basic amino acids, arginine is preferred when zinc gluconate is injected into the testis or epididymis.

In neutralizing the mineral salts such as zinc gluconate, it is preferred that the mineral salts and the amino acid be present in substantially equimolar amounts. Suitable formulations for inhibiting the generation, maturation, motility and viability of sperm are formed with a molar ratio of mineral salt such as zinc gluconate to amino acid such as arginine from about 0.05M:2.0M to about 2.0M:0.05M, preferably from about 0.05 M:0.3 M to about 0.3M:0.05M and most preferably from about 0.1 M:0.2 M to about 0.2M:0.1 M and neutralized to a pH in the range from about 6.0 to about 8.0, preferably from about 6.5 to about 7.5 and most preferably 7.0.

When the biologically active mineral salt is near neutral in water solution without neutralization, such as zinc acetate and calcium acetate, the salts are effectively present in an amount from about 0.05M to about 2.0M, preferably from about 0.05M to about 0.3M and most preferably from about 0.1 M to about 0.2M.

In some instances, it is advantageous to administer the cell permeable physiologically acceptable water soluble minerals in a sustained release form. In such case they may be combined with polymers or microspheres formed of aloe vera muccopolysaccharides or the like as a vehicle to make the compound long-acting for cervical and uterine contraception and to enable the mixture to adhere to the fallopian tubes for fallopian tube contraception.

Cell permeable physiologically acceptable water soluble minerals have the potential of being a post-coital method of contraception by diffusing them into the uterus through the vagina with microspheres providing for sustained release for 4–5 days after coitus. Since fertilization and implantation usually requires about 5 days, a compound having such properties can stop implantation of the fertilized egg and be a major breakthrough in the field of fertility control.

The following examples illustrate the invention.

EXAMPLE 1

Twenty-five sexually mature male rats were divided into the following five groups:

1. Control
2. Injected intratesticularly with 0.1 M (5%) Zinc Gluconate
3. Injected intratesticularly with 0.1 M (1.46%) L-Lysine
4. Injected intratesticularly with 0.1 M (5%) Zinc Gluconate and 0.1 M (1.46%) L-Lysine
5. Injected intratesticularly with 0.1 M (5%) Zinc Gluconate and 0.1 M (1.74%) Arginine After sixty days, the animals were sacrificed and body, testis, epididymis and prostate weights determined. The results are shown in Tables I–VI. Histology photographs were also made of testicular sections. The treatment applied in Group 5 produced the most significant change in decreasing the size of the reproductive organs. The results also show that arginine is a better permeation enhancer for zinc gluconate in the testis than lysine.

TABLE I

| | | % WEIGHT DECREASES FROM CONTROL | | |
|---|---|---|---|---|
| Group | pH | TOTAL TESTIS | TOTAL EPIDIDYMIS | PROSTATE |
| Group 2 - Rats Injected with 0.1M (5%) Zinc Gluconate | 5.5 | 68.98 | 45.10 | 25.67 |
| Group 3 - Rats Injected with 0.1M (1.46%) L-Lysine | 7.4 | 20.49 | 16.16 | 23.31 |
| Group 4 - Rats Injected with 0.1M (5%) Zinc Gluconate and 0.1M (1.46%) L-Lysine | 7.0 | 67.97 | 47.92 | 25.67 |
| Group 5 - Rats Injected with 0.1M (5%) Zinc Gluconate and 0.1M (1.74%) Arginine | 7.0 | 80.50 | 58.35 | 43.40 |

TABLE II

GROUP 1
CONTROL RATS
(Weight in Grams)

| Animal No. | Final body Weight | Testicle Weights | | | Epididymis Weights | | | S.V. | Prostate |
|---|---|---|---|---|---|---|---|---|---|
| | | Right | Left | Total | Right | Left | Total | | |
| 254 | 501 | 1.648 | 1.684 | 3.332 | 0.588 | 0.617 | 1.205 | 0.774 | 1.514 |
| 255 | 470 | 1.706 | 1.740 | 3.446 | 0.638 | 0.609 | 1.247 | 0.757 | 1.706 |
| 256 | 608 | 1.972 | 2.050 | 4.022 | 0.680 | 0.631 | 1.311 | 0.690 | 1.490 |
| 257 | 524 | 1.755 | 1.729 | 3.484 | 0.636 | 0.686 | 1.322 | 0.812 | 1.616 |
| 258 | 516 | 1.774 | 1.705 | 3.479 | 0.675 | 0.614 | 1.289 | 0.826 | 1.291 |
| X | 523.8 | 1.771 | 1.782 | 3.553 | 0.643 | 0.631 | 1.275 | 0.772 | 1.523 |
| S. D. | 51.4 | 0.122 | 0.152 | 0.270 | 0.037 | 0.032 | 0.048 | 0.054 | 0.156 |
| S. E. | 23.0 | 0.055 | 0.068 | 0.121 | 0.017 | 0.014 | 0.022 | 0.024 | 0.070 |

TABLE III

GROUP 2
RATS INJECTED WITH 0.1M (5%) ZINC GLUCONATE
(Weight in Grams)

| Animal No. | Final Body Weight | Testicle Weights | | | Epididymis Weights | | | S.V. | Prostate |
|---|---|---|---|---|---|---|---|---|---|
| | | Right | Left | Total | Right | Left | Total | | |
| 234 | 578 | 0.504 | 0.585 | 1.089 | 0.340 | 0.295 | 0.635 | 0.512 | 1.102 |
| 235 | 544 | 0.324 | 0.761 | 1.085 | 0.332 | 0.338 | 0.670 | 0.549 | 1.080 |
| 236 | 499 | 0.235 | 0.451 | 0.686 | 0.200 | 0.245 | 0.445 | 0.271 | 0.701 |
| 237 | 563 | 0.930 | 0.713 | 1.643 | 0.522 | 0.499 | 1.021 | 0.561 | 1.496 |
| 238 | 532 | 0.436 | 0.575 | 1.011 | 0.330 | 0.398 | 0.728 | 0.601 | 1.280 |
| X | 543.2 | 0.486 | 0.617 | 1.103 | 0.345 | 0.355 | 0.700 | 0.499 | 1.132 |
| S. D. | 30.3 | 0.269 | 0.123 | 0.344 | 0.115 | 0.098 | 0.209 | 0.131 | 0.293 |
| S. E. | 13.6 | 0.120 | 0.055 | 0.154 | 0.051 | 0.044 | 0.093 | 0.059 | 0.131 |

TABLE IV

GROUP 3
RATS INJECTED WITH 0.1M (1.46%) L-LYSINE
(Weight in Grams)

| Animal No. | Final Body Weight | Testicle Weights | | | Epididymis Weights | | | S.V. | Prostate |
|---|---|---|---|---|---|---|---|---|---|
| | | Right | Left | Total | Right | Left | Total | | |
| 239 | 555 | 1.577 | 1.462 | 3.039 | 0.557 | 0.533 | 1.090 | 0.557 | 1.035 |
| 240 | 516 | 1.501 | 1.452 | 2.953 | 0.557 | 0.542 | 1.099 | 0.504 | 1.142 |
| 241 | 555 | 1.513 | 1.529 | 3.042 | 0.571 | 0.599 | 1.170 | 0.750 | 1.477 |
| 242 | 520 | 1.448 | 1.313 | 2.761 | 0.590 | 0.457 | 1.047 | 0.612 | 1.027 |
| 243 | 465 | 1.137 | 1.327 | 2.464 | 0.454 | 0.485 | 0.939 | 0.505 | 1.160 |
| X | 522.2 | 1.435 | 1.417 | 2.825 | 0.546 | 0.523 | 1.069 | 0.586 | 1.168 |
| S. D. | 37.0 | 0.173 | 0.093 | 0.245 | 0.053 | 0.055 | 0.085 | 0.102 | 0.183 |
| S. E. | 16.5 | 0.077 | 0.042 | 0.110 | 0.024 | 0.025 | 0.038 | 0.046 | 0.082 |

TABLE V

GROUP 4
RATS INJECTED WITH 0.1M (5%) ZINC GLUCONATE AND 0.1M (1.46%) L-LYSINE
(Weight in Grams)

| Animal No. | Final Body Weight | Testicle Weights | | | Epididymis Weights | | | S.V. | Prostate |
|---|---|---|---|---|---|---|---|---|---|
| | | Right | Left | Total | Right | Left | Total | | |
| 244 | 588 | 0.484 | 0.565 | 1.049 | 0.237 | 0.319 | 0.556 | 0.518 | 1.158 |
| 245 | 548 | 0.667 | 0.437 | 1.104 | 0.320 | 0.305 | 0.625 | 0.647 | 1.266 |
| 246 | 498 | 0.516 | 0.582 | 1.098 | 0.330 | 0.271 | 0.601 | 0.557 | 0.864 |
| 247 | 539 | 0.382 | 0.899 | 1.281 | 0.326 | 0.476 | 0.802 | 0.792 | 1.271 |
| 248 | 548 | 0.669 | 0.487 | 1.156 | 0.372 | 0.366 | 0.738 | 0.651 | 1.100 |
| X | 544.2 | 0.544 | 0.594 | 1.138 | 0.317 | 0.347 | 0.664 | 0.633 | 1.132 |
| S. D. | 32.1 | 0.124 | 0.180 | 0.089 | 0.049 | 0.080 | 0.102 | 0.106 | 0.166 |
| S. E. | 14.3 | 0.055 | 0.081 | 0.040 | 0.022 | 0.036 | 0.046 | 0.047 | 0.074 |

TABLE VI

GROUP 5
RATS INJECTED WITH 0.1M (5%) ZINC GLUCONATE AND 0.1M (1.74%) ARGININE
(Weight in Grams)

| Animal No. | Final Body Weight | Testicle Weights | | | Epididymis Weights | | | S.V. | Prostate |
|---|---|---|---|---|---|---|---|---|---|
| | | Right | Left | Total | Right | Left | Total | | |
| 249 | 480 | 0.180 | 0.254 | 0.434 | 0.153 | 0.104 | 0.257 | 0.088 | 0.247 |
| 250 | 520 | 0.344 | 0.145 | 0.489 | 0.280 | 0.240 | 0.520 | 0.341 | 0.777 |
| 251 | 501 | 0.387 | 0.311 | 0.698 | 0.206 | 0.238 | 0.444 | 0.380 | 0.830 |
| 252 | 562 | 0.492 | 0.480 | 0.972 | 0.395 | 0.399 | 0.794 | 0.603 | 1.571 |
| 253 | 519 | 0.324 | 0.550 | 0.874 | 0.311 | 0.330 | 0.641 | 0.442 | 0.884 |
| X | 576.4 | 0.345 | 0.348 | 0.693 | 0.269 | 0.262 | 0.531 | 0.371 | 0.862 |
| S. D. | 139.5 | 0.113 | 0.166 | 0.234 | 0.094 | 0.111 | 0.203 | 0.187 | 0.472 |
| S. E. | 62.4 | 0.051 | 0.074 | 0.105 | 0.042 | 0.050 | 0.091 | 0.084 | 0.211 |

EXAMPLE 2

Ten sexually mature male rats were injected intra-epididymally into the head of the epididymis with 0.05 ml of a solution composed of 0.1 M (5%) zinc gluconate and 0.1 M (1.74%) arginine neutralized with hydrochloric acid to pH 7.0. The ten treated animals were examined for changes in testicular function. Spermatogenesis was normal and there was no significant change in testosterone blood levels. Each treated male was mated with five female rats but no pregnancy occurred.

Figure 2:
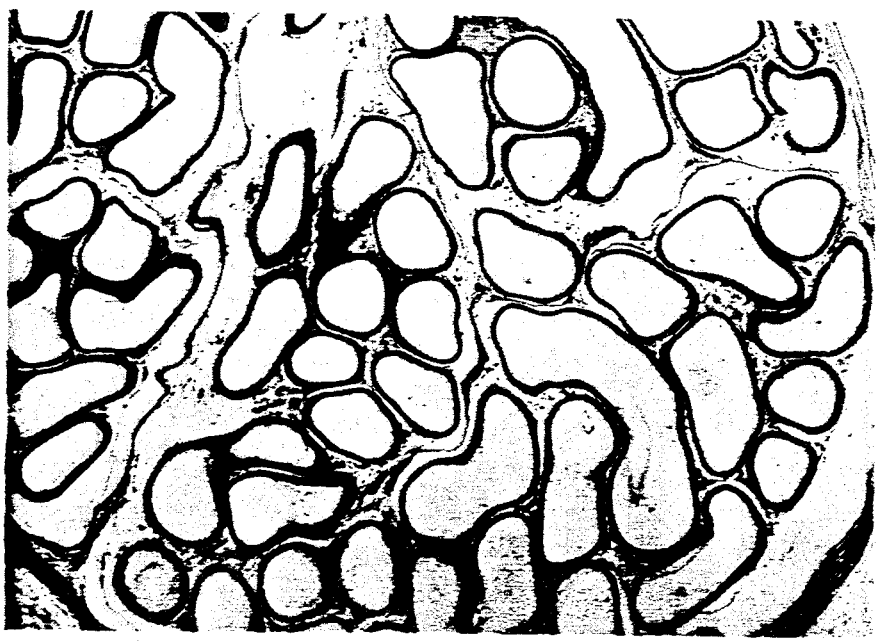

The animals were sacrificed and histology photographs were taken of epididymal sections from the treated animals, a typical one of which is shown in FIG. 2. FIG. 1 is a histology photograph of an epididymal section from a control animal. As shown in FIG. 1, the ductuli efferentes in the epididymides were lined by a tall columnar epithelium and all tubules contained sperm. The average diameter of the lumen of the ductuli efferentes was approximately 100-125 microns. The coils of the ductus epididymis in the epididymides were lined by a tall pseudostratified epithelium and all coils contained sperm. The average diameter of the lumen of the coils of the ductus epididymis was approximately 250 microns. The lining epithelium of the ductus epididymis varied little in height from head to tail. The epithelium lining the ductus deferens was a low columnar epithelium. The average diameter of the coils in the ductus deferens was approximately 400 microns. All coils of the ductus deferens contained sperm.

In the treated animals, on gross observation the epididymis was approximately normal size. As shown in FIG. 2, the ductuli efferentes were lined by a tall columnar epithelium and did not contain any sperm. There was an increase in the interductal connective tissue. The average lumen diameter was approximately 50 microns. The coils of the ductus epididymis were lined by a tall pseudostratified epithelium. None of the coils of the ductus epididymis contained sperm. All of the coils contained amorphous pink secretory material. There was an increase in the intercoil connective tissue in all parts of the epididymis. The epithelium increased in height in the coils of the epididymis from the head to the tail. The ductus deferens was lined by a low columnar epithelium. None of the coils of the ductus deferens contained sperm. Its diameter was 200 microns. All of the coils contained amorphous pink material or necrotic debris.

Until recently, the epididymis was considered a passive channel through which the spermatozoa could leave the seminiferous tubules in order to be stored before being ejaculated. Recently, it has been recognized that during the time of their passage though the epididymis the spermatozoa change from functionally immature cells unable to fertilize an egg to cells with full fertilizing capacity, thus achieving complete maturation, and therefore that the epididymis has a crucial role in the physiology of male reproduction. This observation has focused interest on the epididymis as a possible target for pharmacological male contraception.

The process of sperm maturation requires a cooperative interaction between the sperm and the epididymal epithelium. The morphological and biochemical modifications occurring in the spermatozoa seem to be mediated by secretory products of the epididymis. A number of epididymal secretory glycoproteins have been identified in the epididymal tissue and fluid of the rat, rabbit, hamster and bull. The protein synthesis in the epididymis shows regional differences, which parallel the morphological changes occurring in the luminal sperm. The greatest activity of the protein synthesis machinery is present in the initial segment, i.e. head or caput, of the epididymis, where the spermatozoa undergo the most dramatic morphological and biochemical changes. After being produced in the caput segment of the epididymis, these proteins interact with and remain attached to spermatozoa as the cells are transported along the duct.

Histochemistry which was done on treated rats in a follow-up indicated that the glycoprotein coating the sperm had been significantly decreased as compared to the control thus inhibiting sperm maturation which is necessary in order for sperm to penetrate and fertilize an egg. Hence the method described in this example achieves male sterilization without affecting spermatogenesis and hormone (testosterone) production in the testes.

EXAMPLE 3

Twenty-one sexually mature mixed breed dogs having ejaculate containing 150 million/ml to 200 million/ml sperm were divided into three groups:
1. Control dogs
2. Dogs injected intratesticularly with 1.5 ml of 0.1 M (5%) Zinc Gluconate and 0.1 M (1.74%) Arginine neutralized with Hydrochloric Acid to pH 7.0
3. Dogs injected into the caudal epididymis with 0.5 ml of 0.1 M (5%) Zinc Gluconate and 0.1M (1.74%) Arginine neutralized with Hydrochloric Acid to pH 7.0.

After injection, the dogs acted and ate normally. One week after treatment, sperm motility was zero and the sperm was broken. Four semen collections performed during a three-month period after treatment revealed the following:

Group 2. In four animals, no fluid was obtained and the animals were dry. Three animals had 1 ml of ejaculate or less and no sperm were found in the ejaculate. Collectively, these results are an indication of the drying effect on the prostate and fluid and on the suppression of spermatogenesis.

Group 3. All animals ejaculated fluid but there were no sperm, only cell debris. This is an indication that the route of administration affects maturation of sperm without affecting testosterone level and the prostate.

When zinc tannate was used in place of neutralized zinc gluconate with arginine, the dogs had to be restrained with foam collars to prevent them from licking and biting their testicles. Sperm condition after treatment was like that reported with neutralized zinc gluconate with arginine but the animals suffered more pain or discomfort.

EXAMPLE 4

Zinc tannate is a proven chemical sterilant when it is injected into the testis of bulls (U.S. Pat. Nos. 4,156,427 and 4,339,438). Animals treated with zinc tannate have difficulty walking for about twenty-four hours after treatment and solutions of zinc tannate are not stable to heat and light under ambient conditions for more than about six months. These facts have limited the marketability of zinc tannate as a chemical sterilant.

In work reported in Example 1, the combination of neutralized zinc gluconate with arginine was demonstrated as very effective at decreasing the size of the reproductive organs. The experiment which is reported in this example was conducted to determine whether the combination of neutralized zinc gluconate with arginine is as effective as zinc tannate at inhibiting spermatogenesis and whether animals treated with the combination experience less morbidity.

For this example, twenty weaned bulls weighing about 500 lbs each were divided into four groups:
1. Control bulls
2. Bulls castrated with a knife
3. Bulls injected intratesticularly with 5-7 ml of Zinc Tannate (9%), pH 3.5
4. Bulls injected intratesticularly with 5-7 ml of 0.2M (10%) Zinc Gluconate and 0.2M (3.48%) Arginine neutralized with Hydrochloric Acid to pH 7.0

Before treatment, the body weight of each bull was determined, a blood sample taken and the testis circumference measured. For the purpose of following their reaction, the animals were marked with different colored ear tags. The bulls in Group 1 were given orange ear tags, Group 2 were marked with brown ear tags, Group 3 with green tags and Group 4 with yellow tags.

The animals with yellow ear tags (Group 4) were the first to show some discomfort after treatment by lying down, stretching and walking somewhat spraddle legged indicating that the sterilant permeated faster than the sterilant in Group 3. This activity began 30 minutes to 1 hour after injection but by 6-8 hours after injection the animals had only slight difficulty in walking.

The same type of reaction but much more severe began in the animals with green tags approximately 45 minutes to 1 hour later than the animals with yellow tags. All of the animals in Group 3 walked with a stilted gait that extended to 24 hours in two animals and 48 hours in three animals.

When observed at 24 hours after treatment, the swelling of the animals with yellow tags was about ⅔ of that of the animals with green tags and their pain response was ⅓ to ⅔ that of the green. The animals in both groups recovered after 2 days and no abnormality was observed in their feeding behavior throughout the treatment.

Four months after treatment, the control animals had 150 million/ml to 280 million/ml sperm. The animals in the treatment groups had zero sperm. These results indicate that neutralized zinc gluconate with arginine is as effective as zinc tannate as a chemical sterilant. It has several advantages over zinc tannate, however, because it significantly reduces the morbidity and reaction of the animals to the injection. In addition, solutions of neutralized zinc gluconate with arginine are stable over extended periods of time and can even be autoclaved.

EXAMPLE 5

Various solutions as shown in the following table were tested for effectiveness as a spermicide. Human males participating in this study were fertile semen donors selected after appropriate screening. One specimen from each of three males was used in this study. Specimens were collected by masturbation following three days abstinence. Following collection, specimens were incubated at 37 degrees C. for 15-30 minutes to allow for liquefaction. Semen volume, sperm density and motility percentage were assessed using a light microscope and a Makler Chamber (Jequier, A. and Crich, J.: Sperm count and assessment of sperm movements. In: *Semen Analysis—A Practical Guide,* A. Jequier and J. Crich, Eds., The Alden Press, Great Britain, 1986, p. 50). Motility of sperm were graded based on forward progression and a scale of 1+ (slowest) to 4+ (fastest).

For the data reported below, refrigerated spermicide solutions were kept at room temperature for 15 minutes to reach the same temperature as semen. An equal volume (0.5 ml) of semen and spermicide were mixed and this was considered 0 time.

| EFFECT OF SPERMICIDAL SOLUTIONS ON SPERM MOTILITY | | | | | | |
|---|---|---|---|---|---|---|
| Solutions | pH | Male # | Initial Motility and Grade | 1 Minute | 10 Minutes | 30 Minutes |
| 2% Zinc Acetate | 7.00 | 1 | 74% 3+ | 0% | 0% | 0% |
| | | 2 | 85% 3+ | 0% | 0% | 0% |
| | | 3 | 78% 3+ | 0% | 0% | 0% |
| 2% Calcium Acetate | 7.00 | 1 | 75% 3+ | 0% | 0% | 0% |
| | | 2 | 80% 3+ | 0% | 0% | 0% |
| | | 3 | 85% 4+ | 0% | 0% | 0% |
| 2% Zinc Gluconate pH adjusted to 7.00 with 5.0 N NaOH | 7.00 | 1 | 74% 3+ | 0% | 0% | 0% |
| | | 2 | 85% 3+ | 0% | 0% | 0% |
| | | 3 | 78% 3+ | 0% | 0% | 0% |
| 2% Zinc Gluconate | 5.62 | 1 | 65% 3+ | 29% 2+ | 20% 1+ | 15% 1+ |
| | | 2 | 75% 4+ | 35% 2+ | 28% 1+ | 20% 1+ |
| | | 3 | 70% 3+ | 28% 2+ | 22% 1+ | 18% 1+ |

From the above, it is seen that zinc gluconate adjusted to pH 7.0 with sodium hydroxide is as effective as zinc acetate and calcium acetate as a spermicide while having the advantage of being neutral and therefore useful as a vaginal contraceptive. It is also seen that zinc gluconate in its acidic form is not as effective as when it is neutralized to pH 7.0. In addition, zinc gluconate in its acidic form does not meet the criteria for spermicidal agents recognized internationally which require the pH of the spermicide to be between 6.0 and 7.5 in order to be effective since the vagina is acidic while the pH of sperm is alkaline or neutral.

As various changes could be made in the above methods and products without departing from the scope of the invention, it is intended that all matter contained in the above description shall be interpreted as illustrative and not in a limiting sense.

What is claimed:

1. A method of inhibiting generation, maturation, motility or viability of sperm in a reproductive tract of an animal comprising applying in said reproductive tract an aqueous solution of a mineral gluconate salt and an amino acid capable of forming the solution, said aqueous solution neutralized to a pH in the range of 6.0 to 7.5 and applied in an amount effective to inhibit generation, maturation, motility or viability of sperm in the reproductive tract and said mineral gluconate salt and said amino acid being present in substantially equal molar amounts at a concentration in the range from about 0.05 M to about 2.0 M.

2. The method of claim 1 wherein the concentration of the mineral gluconate salt and the amino acid is from about 0.05 M to about 0.3 M.

3. The method of claim 1 wherein the concentration of the mineral gluconate salt and the amino acid is from about 0.1 M to about 0.2 M.

4. The method of claim 1 wherein the mineral gluconate salt is zinc gluconate.

5. The method of claim 4 wherein the amino acid is a basic amino acid selected from the group consisting of lysine, arginine, histidine and mixtures thereof.

6. A method of inhibiting generation or maturation of sperm in a testis or epididymis of a male animal comprising applying in said testis or epididymis an aqueous solution of zinc gluconate and an amino acid capable of forming the solution, said aqueous solution neutralized to a pH in the range of 6.0 to 7.5 and applied in an amount effective to inhibit generation or maturation of sperm in the testis or epididymis and said zinc gluconate and said amino acid being present in substantially equal molar amounts at a concentration in the range from about 0.05 M to about 2.0 M.

7. The method of claim 6 wherein the concentration of the zinc gluconate and the amino acid is from about 0.05 M to about 0.3 M.

8. The method of claim 6 wherein the concentration of the zinc gluconate and the amino acid is from about 0.1 M to about 0.2 M.

9. The method of claim 6 wherein the amino acid is a basic amino acid selected from the group consisting of lysine, arginine, histidine and mixtures thereof.

10. The method of claim 9 wherein the basic amino acid is arginine.

11. A method of inhibiting motility or viability of sperm in a vagina, cervix, uterus or fallopian tube of a female animal comprising applying in said vagina, cervix, uterus or fallopian tube an aqueous solution of a mineral gluconate salt and an amino acid capable of forming the solution, said aqueous solution neutralized to a pH in the range 6.0 to 7.5 and applied in an amount effective to inhibit motility or viability of sperm in said vagina, cervix, uterus or fallopian tube and said mineral gluconate salt and said amino acid being present in substantially equal molar amounts at a concentration in the range from about 0.05 M to about 2.0 M.

12. The method of claim 11 wherein the concentration of the mineral gluconate salt and the amino acid is from about 0.05 M to about 0.3 M.

13. The method of claim 11 wherein the concentration of the mineral gluconate salt and the amino acid is from about 0.1 M to about 0.2 M.

14. The method of claim 11 wherein the mineral gluconate salt is zinc gluconate.

15. The method of claim 14 wherein the amino acid is a basic amino acid selected from the group consisting of lysine, arginine, histidine and mixtures thereof.

* * * * *